(12) United States Patent
Senn et al.

(10) Patent No.: US 6,322,358 B1
(45) Date of Patent: Nov. 27, 2001

(54) CURING DEVICE FOR LIGHT-INDUCED CURING OF DENTAL MATERIALS

(75) Inventors: Bruno Senn, Buchs; Gregor Fritsche; Gottfried Rohner, both of Altstätten, all of (CH)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 09/260,400

(22) Filed: Mar. 1, 1999

Related U.S. Application Data
(60) Provisional application No. 60/084,216, filed on May 5, 1998.

(30) Foreign Application Priority Data

Mar. 9, 1998 (DE) .............................................. 198 10 042

(51) Int. Cl.[7] .................................................... A61C 1/00
(52) U.S. Cl. ............................................................. 433/29
(58) Field of Search ................... 433/28, 29, 77; 362/183, 804

(56) References Cited

U.S. PATENT DOCUMENTS

| 5,147,204 | * | 9/1992 | Patten et al. ........................ 433/29 X |
| 5,324,197 | * | 6/1994 | Shain et al. ............................ 433/29 |
| 5,332,392 | * | 7/1994 | Bierbaum et al. ................. 433/79 X |
| 5,397,892 | * | 3/1995 | Abdelqader ........................ 433/29 X |

FOREIGN PATENT DOCUMENTS

| 9212892 | 1/1993 | (DE) . |
| 0568800 | 11/1993 | (EP) . |
| 0166364 | 1/1996 | (EP) . |

OTHER PUBLICATIONS

Visilux 2 Field Service Handbook, 3M Company, pp. 2–1 to 2–5, 5–1 to 5–2, 6–1 to 6–5. December 1990.

* cited by examiner

Primary Examiner—Nicholas D. Lucchesi
(74) Attorney, Agent, or Firm—John C. Thompson; Alan S. Korman

(57) ABSTRACT

A cutting device for light-induced curing of dental materials includes a hand-held apparatus containing a light source whereby the hand-held apparatus is pistol-shaped and comprises a main body and a grip connected to the main body. A cable connects the grip of the hand-held apparatus to a supply station. A support for receiving the hand-held apparatus is provided. The support is detachably connected to the supply station or a stand such that the support in which the hand-held apparatus is received is storable at the supply station or separate from the supply station.

18 Claims, 3 Drawing Sheets

US 6,322,358 B1

CURING DEVICE FOR LIGHT-INDUCED CURING OF DENTAL MATERIALS

This application claims benefit of Provisional Appl. 60/084,216 filed May 5, 1998.

BACKGROUND OF THE INVENTION

The present invention relates to curing device, especially for light-induced curing of dental materials, having substantially a pistol-shape with a grip whereby the grip is connected by a cable to a supply station and whereby the supply station has a support for supporting the curing device.

Such a light curing device, in the following referred to as hand-held apparatus, is known from European patent application 0 166 364 or German Gebrauchsmuster 92 12 892. These known solutions have a cable connection between the grip of the substantially pistol-shaped hand-held apparatus and the supply station. For ergonomic reasons, the cable exits the hand-held apparatus usually at the lower end of the grip in order to prevent that the cable will be a nuisance when manipulating the device in the vicinity of a patent's mouth.

The supply station has a support for supporting the hand-held apparatus which support receives the grip of the hand-held apparatus. While such a support for a hand-held apparatus operated by batteries, as known from European patent application 568 800, can be realized without problems, the more powerful cable-supplied version of a hand-held apparatus, that is independent of battery operation, requires special measures at the support in order to accommodate the cable connection for such plug-in supports.

German Gebrauchsmuster 95 12 892 therefore provides special slots. However, this requires the cable to be inserted exactly at this location. This complicated insertion has already been realized in the known Gebrauchsmuster so that instead of one slot two slots are provided which both are suitable for extending the cable therethrough.

Even though these slots provide a plurality of insertion possibilities, i.e., in the case of two slots two insertion possibilities, the insertion of the grip into this location at the support requires a relatively great manipulation precision and especially requires the careful attention of the dentist. However, such an attention to detail is undesirable for such hand-held apparatus because the dentist should be able to concentrate fully on the actual dental work without having to attend to special manipulation problems for the dental apparatus he uses.

It is thus understandable that such hand-held apparatus are carelessly placed onto the treatment table or an auxiliary tray where the hand-held apparatus is unprotected. The sensitive end of the light guide is exposed, and, when accidentally catching the connecting cable between the supply station and the hand-held apparatus, the apparatus can be easily pulled off the table and damaged, especially since the surfaces of the hand-held apparatus as well as of the table or tray are usually very smooth for reasons of hygiene.

Accordingly, it is an object of the present invention to provide a light curing device of the aforementioned kind which is improved with respect to manipulation and storage so as to be accepted by dentists as well as with respect to ergonomic aspects.

SUMMARY OF THE INVENTION

A curing device for light-induced curing of dental materials according to the present invention is primarily characterized by:

a hand-held apparatus containing a light source;

the hand-held apparatus being pistol-shaped comprising a main body and a grip connected to the main body;

a cable connected to the grip for connecting the hand-held apparatus to a supply station;

a support for receiving the hand-held apparatus;

the support detachably connectable to the supply station or a stand such that the support in which the hand-held apparatus is received is storable at the supply station or separate from the supply station.

Advantageously, the support has a bracket for supporting at least a portion of the main body in front of the grip.

Preferably, the bracket provides slanted supporting surfaces along both sides of the main body and beneath the main body.

The bracket is preferably comprised of a bent wire and has two ends insertable into a holder at the supply station or into the stand.

The cable preferably has plugs for detachably connecting the cable to the supply station and the grip.

The cable is preferably provided in different lengths such that an appropriate length is selectable as needed.

The bracket preferably includes two lateral portions and a curved center portion positioned between the lateral portions.

The bracket is advantageously comprised of a bent wire and has two lower ends. When viewed from the ends, the bracket has two parallel, upwardly extending legs and first transition portions extending forwardly in a longitudinal direction of the main body. The lateral portions are connected to the first transition portions and extends to the rear of the main body parallel to the longitudinal direction. The bracket includes two second transition portions extending downwardly and toward one another and connecting the lateral portions and the central curved portion.

The lateral portions preferably have a length between the first and second transition portions that is greater than the width of the grip in the longitudinal direction.

The length of the valor portions is approximately half the length of the main body.

The grip is preferably received and partly surrounded by the central curved portion.

Advantageously, the hand-held apparatus is positionable in the support only in one defined position and the hand-held apparatus, when incorrectly placed into the support, will right itself relative to the support in order to assume the defined position.

Expediently, the hand-held apparatus has a light guide having an end portion angled downwardly. The end portion of the light guide has an end facing the surface of the supply station and positioned directly adjacent to that surface when the hand-held apparatus is received in the support inserted into the holder.

Between the surface of the supply station and the end face of the light guide a safety distance of 1 cm to 2 cm is provided.

The support, when inserted into the stand, is placeable onto a table.

The stand has a support plate extending beneath the end portion of the light guide of the curing device when received in the support.

The support plate has a clamping device for securing the support plate at a table.

The present invention also relates to an apparatus for light-induced curing of dental materials wherein the apparatus comprises a supply station and a hand-held apparatus containing a light source. Preferably, the hand-held apparatus is pistol-shaped and includes a main body and a grip connected to the main body. A cable connects the grip of the hand-held apparatus to the supply station. A support for receiving the hand-held apparatus is provided. The support is detachably connectable to the supply station such that the support in which the hand-held apparatus is received is storable at the supply station or separate from the supply station.

According to the present invention, the light curing device is supported in a support at the supply station whereby the support for the light curing device is detachably supported at the supply station and, when needed, can be removed therefrom. The support together with the light curing device can thus be stored separate from the supply station.

According to an especially advantageous embodiment of the invention, the support is embodied such that the hand-held apparatus is supported at least partially by the support in front of the grip whereby it is especially advantageous when the center of gravity of the hand-held apparatus, when supported on the support, is positioned above the support such that a vertical line through the center of gravity is clearly spaced from the edges of the support and extends through the support. Preferably, a slanted position of the hand-held apparatus is provided so that the grip of the hand-held apparatus points toward the user. However, the sensitive light guide is well protected because it extends above the supply station. The angled end portion of the light guide may be facing the supply station and in this manner is especially protected.

Relative to the surface of the supply station, the support together with the light guide and the front end of the hand-held apparatus thus define a triangle whereby the embodiment of the support as a bracket has the additional advantage that the light curing device when furnished with a vibration-sensitive halogen lamp as a light source is essentially dampened even when positioned in the support rather quickly. The light source is thus exposed to vibrations to a lesser extent as compared to a hand-held apparatus that is placed quickly onto a hard surface or inserted with its grip into a support with a fixed bottom portion.

A careful treatment of the light source is also important with respect to dental-techniological reasons. It has been observed that multiple vibrations reduce the service life of the employed halogen light source substantially in the same way as the voltage-controlled switching action of the light source resulting in a high current peak.

Inventively, it is thus advantageous that, when a lamp-protecting switching function for the light source is provided, the conventional service life of the light source can be used to the full extent and that this service life is surprisingly not shortened by vibrations.

Inventively, the support is detachably connected to the supply station. This opens possibilities with respect to separating the support from the supply station and to store the hand-held apparatus at a spacing from the supply station. The dentist is thus able to position the supply station at a remote location, for example, in a covered location so that it is protected from dust. Within his working range, the dentist thus has to deal only with the hand-held apparatus and the support therefor. In this context it is especially favorable to connect the cable by a detachable plug connection to the hand-held apparatus and the supply station because then cables of different lengths can be used in order to provide for a simple adaptation to the respective spacial requirements.

The support for the light curing device may have different shapes and, for example, can be a stand made of plastic or metal. Such a stand can be anchored, for example, in three bores within the supply station and can then be positioned on a table surface. The three-point design ensures secure placement onto flat surfaces. The stand can also have three legs which are elastic and which, when placed onto a surface, will spread. Also, the stand can be provided with a single or multiple legs which allow placement onto a surface.

It is furthermore especially advantageous that the inventive hand-held apparatus can be easily manipulated by the dentist without requiring special attention that would be taken away from the patent in order to be able to carry out the precise manipulation steps for handling the apparatus. When placing the hand-held apparatus onto the support, without the dentist taking special precautions, especially when the support is slanted and provides a substantially V-shaped supporting action for the hand-held apparatus, the hand-held apparatus easily and automatically slides due to the slanted positioning of the support into its defined end position, even when it is placed onto the support in a slightly canted or laterally slightly misaligned manner.

According to a further especially advantageous embodiment it is suggested to embody the support as a bracket which is supported on a stand that is independent of the supply station. This stand can then be connected to a working surface, for example, by clamping screws, and the supply station itself is positioned below the working surface. It is thus out of sight, less susceptible to soiling, and will also not impede other actions to be performed by the dentist In this design the working surface is practically a replacement for the surface of the supply station and thus provides due to its arrangement a protection of the relatively sensitive end portion of the light guide which is therefore less susceptible to soiling.

With the inventive simple and inexpensive means a significant improvement of the manipulation of such light curing devices can be achieved which fulfill to a large degree the requirements of a dental practice.

It is understood that the precise design of the inventive bracket can be adapted as needed to a wide range of specifications.

Preferably, the bracket is comprised of two lateral portions which extend symmetrically to one another and provide a substantially V or V-shaped support surface which is self-centering. The design can expediently be provided such that a threading (catching) of the light guide end portion is no longer possible at one of the lateral portions or the central curved portion, even when the end portion of the light guide is angled or slanted and pointed downwardly.

Preferably, the central curved portion is positioned lower so that the end portion of the light guide cannot catch thereon, even if the hand-held apparatus is inserted carelessly.

While the disclosed embodiments show a shape of the lateral portions that is closed in the forward direction, according to a modified embodiment it is also possible to design the lateral portions such that no forward curved transition portions are provided or to design them such that they extend radially relative to the hand-held apparatus.

While hand-held apparatus with angled light guide end portions conventionally have light guides that are rotatable relative to the apparatus, so that they are useable for light polymerization in the upper jaw as well as in the lower jaw, the light guides at the end of the treatment are sometimes rotated such that the light guide end portions face downwardly. This is the most favorite position with regard to preventing soiling, and in this most common position the inventive design of a light curing device provides a special protection for the end portion of the light guide.

The spacing of the end portion of the light guide to the surface, i.e., to the surface to the supply station or to the working surface, is preferably such that even for a maximum spring action of the bracket and for a respective harsh manipulation of the end portion of the light guide, the end portion is still safely spaced from the surface, while it is advantageous that in the resting and unstressed position of the bracket the end portion of the light guide is at most a few centimeters away from the surface in order to provide especially good protection of the end portion.

According to a further advantageous embodiment of the invention it is suggested that the support is comprised of wire which can be easily cleaned and disinfected and which is easily insertable into the supply station or a stand. If needed, the bracket made of wire can be removed and completely introduced into a disinfection bath. Even when this is not required, the inventive support is any case easy to clean and has no comers that are prone to soiling, as, for example the design of German Gebrauchsmuster 92 12 892.

According to a further especially advantageous aspect of the invention the surface of the supply station is curved. This aesthetically especially pleasing design allows for an alignment of the surface parallel to the end portion of the light guide.

The length of the support is preferably somewhat smaller than the length of the main body of the hand-held apparatus and substantially smaller than the total length of the hand-held apparatus inclusive the light guide. This size consideration allows for a safe supporting action, but provides a compact design of the inventive bracket.

Preferably, the supply station is a flat element having a height so that it fits into the standardized drawers of dental practice furniture. Accordingly, it is possible to position the supply station in such drawers. When removing the cable from the plug-in connection at the supply station, the light curing device and the support for the light curing device can be completely separated from the supply station and can be stored separately.

BRIEF DESCRIPTION OF THE DRAWINGS

The object and advantages of the present invention will appear more clearly from the following specification in conjunction with the accompanying drawings in which.

DESCRIPTION OF PREFERRED EMBODIMENTS

Figure 1:
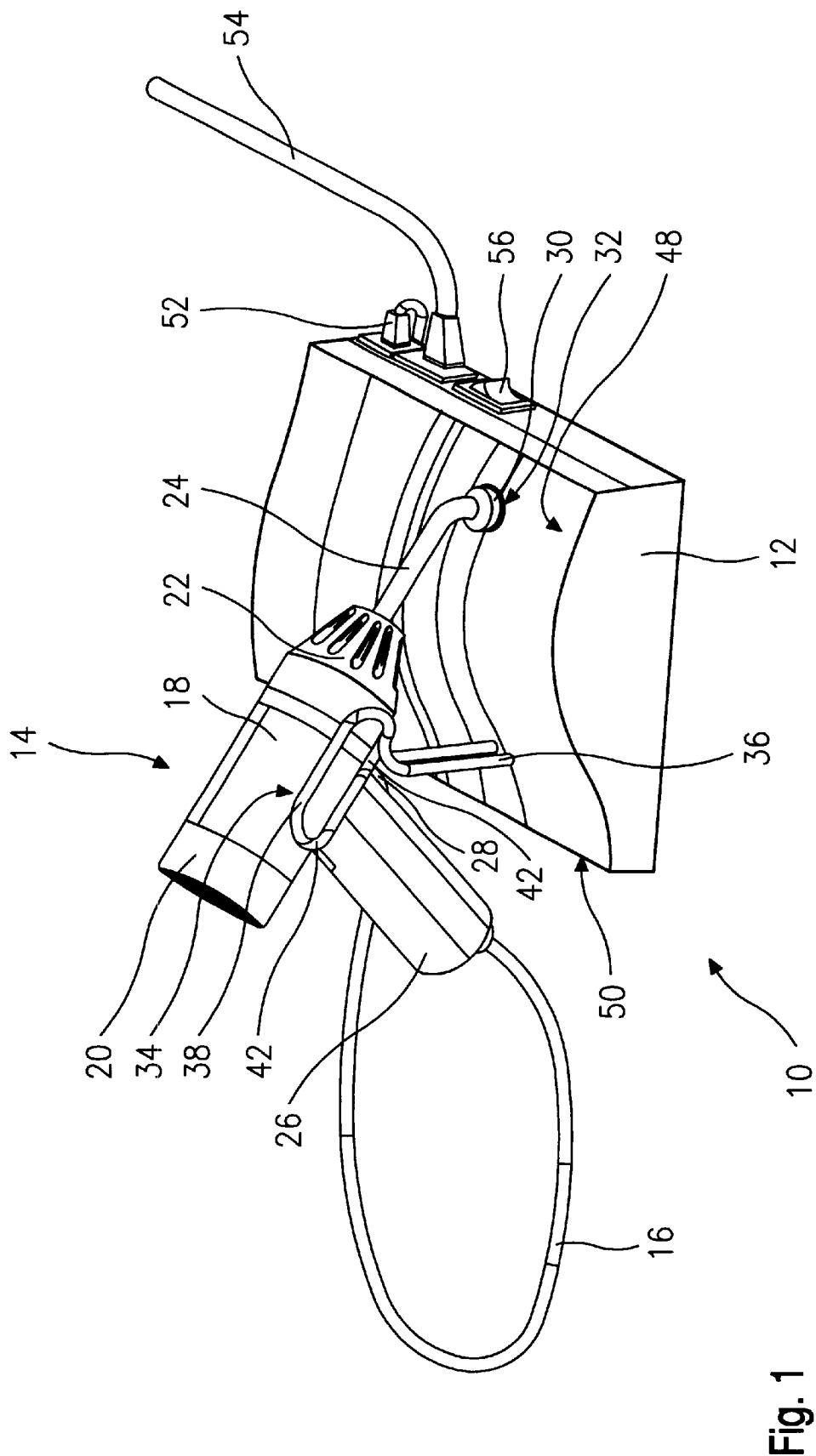
FIG. 1 is a perspective view of an embodiment of the inventive light curing device, showing the hand-held apparatus inserted in the support.
Figure 2:
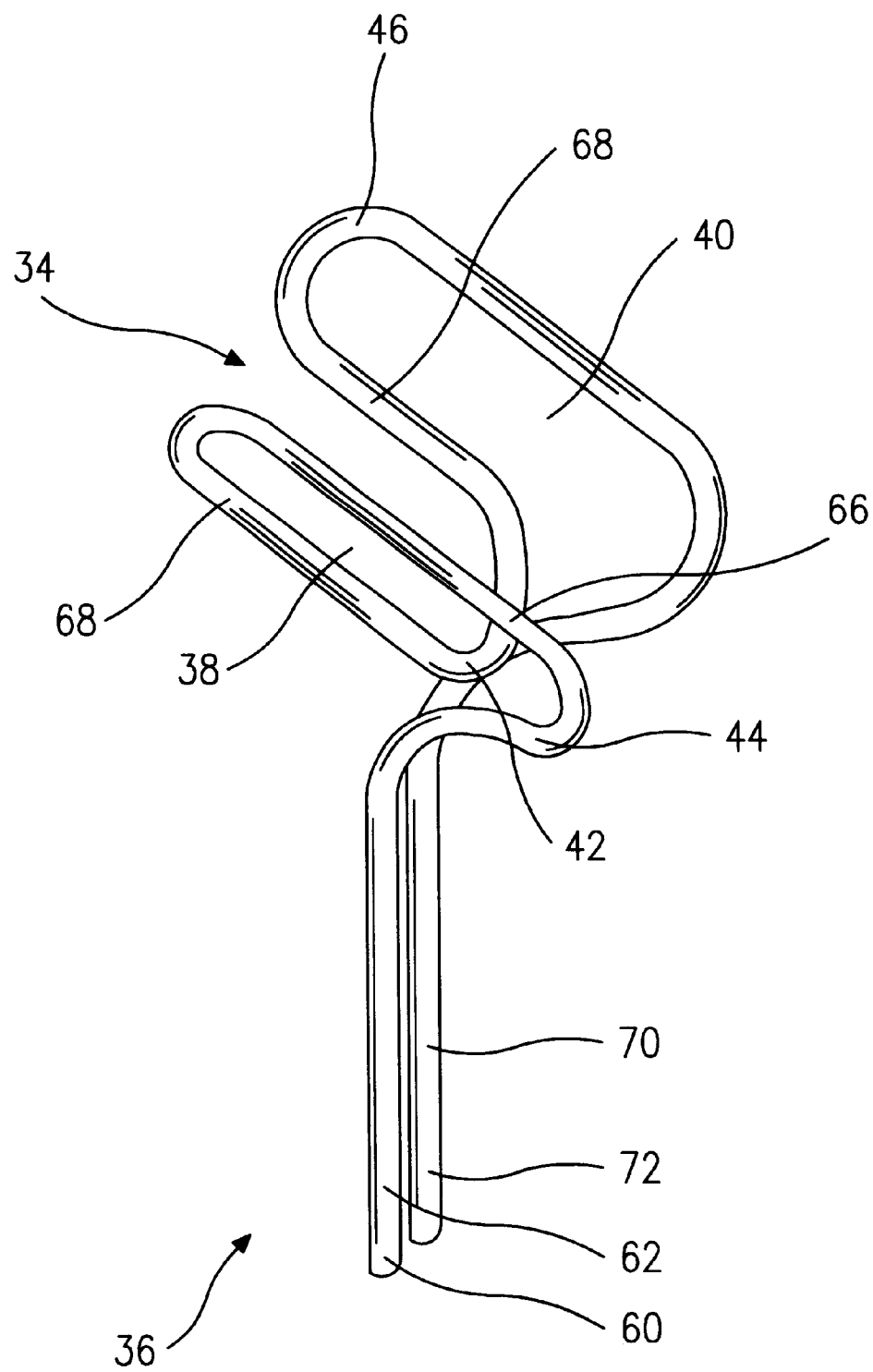
FIG. 2 shows the inventive support in an embodiment comprising a bracket made of wire.
Figure 3:
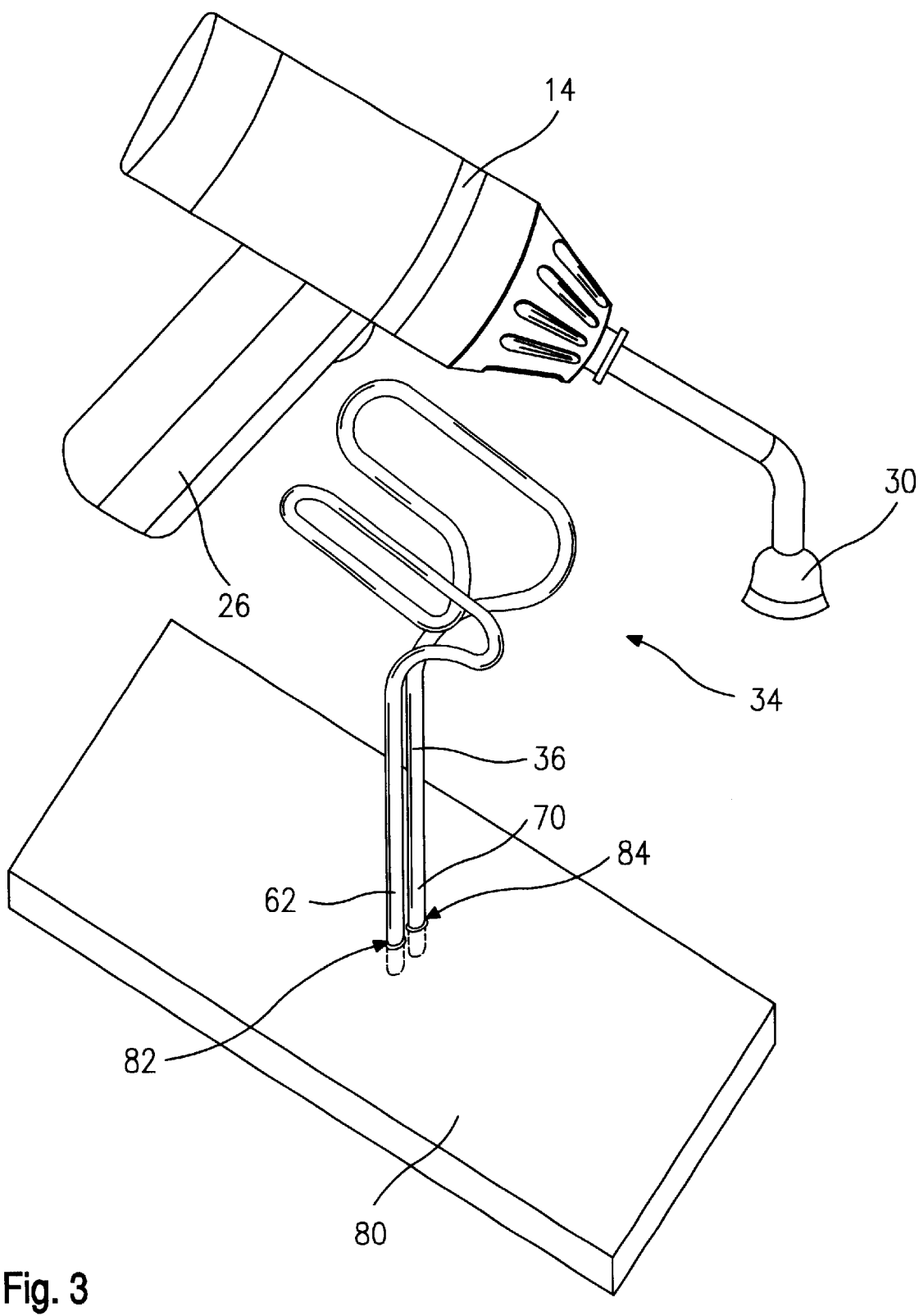
FIG. 3 shows a perspective view of an embodiment of the inventive light curing device in which the support is inserted into a separate stand.

The present invention will now described in detail with the aid of several specific embodiments utilizing FIGS. 1 through 3.

The embodiment of a light curing device 10 represented in FIG. 1 comprises a supply station 12 and a hand-held apparatus 14 connected by cable 16. The cable 16 is provided at both ends with plug connections and is supplied in various precut lengths.

The hand-held apparatus is substantially pistol-shaped. Its main body 18 comprises a substantially cylindrical part 20 ending in a cone 22 and having a transition into a light guide 24.

A grip 26 extends at a slant to the rear and downwardly from the part 20. It is furnished in a manner known per se with a switch 28 for switching on and off the light source contained in the main body 18. The end 30 of the light guide 24 is angled and has an end face 32 which, in the position shown in FIG. 1, points downwardly. Inventively, a support 34 for the hand-held apparatus is provided which, in the shown embodiment, is positioned on the supply station 12. The support 34 has a bracket 36 for receiving the hand-held apparatus 14 whereby the bracket 36 safely supports the main body 18 at the supply station due to its special design.

The bracket 36 has two lateral portions 38 and 40 whereby in FIG. 1 only the lateral portion 38 can be seen while the lateral portion 40 (shown in FIG. 2) in the representation according to FIG. 1 is covered by the main body 18 of the apparatus 14. The lateral portions 38 and 40 are connected to one another by a central curved portion 32. In the position represented in FIG. 1, which is the end position of the hand-held apparatus 14 in the support 34, the central curved portion 42 surrounds the grip 26 on three sides and extends practically over the entire length of the grip, when viewed in the axial or longitudinal direction of the light curing device.

The lateral portions in the shown embodiment are embodied such that to the front and to the rear they have a first and a second transitions 44 and 46, as can be seen especially in FIG. 2.

The supply station 12 has at its surface 48 two bores spaced from one another into which the two ends of the bracket 36 are inserted. Since the bracket 36 during manipulation, i.e., when removing or placing the hand-held apparatus 14, is never loaded with respect to pulling forces, an insertion of the ends of the bracket without snap-connection is sufficient whereby it is understood that, if needed, such a snap-connection could be provided.

The surface 48 of the supply station 12 is of a special design. In a plan view the surface 48 is substantially trapezoidal in shape. The surface 48 in the vicinity of a shorter side of the trapeze has a greater curvature than in the vicinity of the longer side. The curvature of the surface 48 is thus more pronounced at the shorter side than at the longer side whereby a harmonic and uniform transition of the curvature from the short to the long trapeze side is provided. The design is selected such that the supply station 12 based on its surface shape provides the impression of a parallelpiped that is compressed whereby this compression is greater at one side than at the other.

This design is not only aesthetically especially pleasing, but also advantageous in that the electric circuits and the supply for the hand-held apparatus can be without problems housed within the supply station 12. Furthermore, this design in connection with the bracket 36 provides excellent protection of the end face 32. When the bracket 36 at its rear portion is positioned adjacent to the short trapeze side, the hand-held apparatus remains with slightly more than its forward half above the supply station. Accordingly, the light guide 24 does not project forwardly past the front edge 50 of the supply station 12. Instead, the angled end 30 of the light guide 24 ends at a downwardly slanted area of the surface 48 so that the end face 32 extends substantially parallel to the surface 48.

This design allows to position the hand-held apparatus such that the grip 28 is easily accessible since only the supply station 12 is below the grip 26, while the end face 32 is still well protected.

The supply station can be adapted in wide ranges to the respective requirements. While in the shown embodiment a plug-connection 52 for the cable 16 is provided whereby the mains connection 54 as well as the on/off switch 56 are positioned adjacent to one another, it is understood that the arrangement of these connections and operating elements can be provided in any suitable design according to the specific requirements. Also, if needed, venting slots for the optionally needed cooling of a transformer or of the current and voltage control for supplying the hand-held apparatus 14 may be provided, preferably at a vertical wall of the supply station 12. However, the compact design with small surfaces of the inventive supply station 12 is especially preferred and easy to clean.

While the represented embodiment of the inventive light curing device 14 shows a position in which the bracket 36 is inserted into the supply station 12, according to a modified embodiment it is suggested to provide an auxiliary holder which, if needed, may also be the only support or holder. The auxiliary holder is comprised of a bracket 36 according to FIG. 2 which is supported in a suitable manner. For example, the bracket 36 can be inserted into a support plate which extends preferably parallel to the hand-held apparatus 14 and extends to a position below the end portion of the light guide. A respective support plate can be embodied as a cast part and, for example, can be fastened with clamping screws to a treatment table while the supply station 12 is stored, preferably covered, for example, in a drawer.

The preferred embodiment of the inventive bracket 36 can be seen in FIG. 2. From one end 60 of the bracket 36 an upwardly extending leg 62 projects. The upper end of the upwardly extending leg 62 is bent in the forward direction and extends substantially horizontally at a slant to form a front curved transition portion 44. Here the lateral portion 38 begins and the wire is bent by 180° to the rear at the this transition portion 44. The main leg of the lateral portion 38 extends not horizontally but at a slant upwardly, according to the position of the hand-held apparatus 14 of the support 34.

At the rear end of the main leg 66, the lateral portion 38 has a rearward curved transition portion 46 which is bent 180° so that the wire extends again in the forward direction parallel to the main leg 62 and provides an auxiliary leg 68 of the lateral portion 38.

The auxiliary leg 68 extends substantially into the area of the upward portion of the leg 62 and it is then bent toward the central curved portion 42. The central curved portion 42 extends at a slant downwardly so that the grip 26 of the hand-held apparatus 14 is preferably positive-lockingly, with a slight wedging action, received between the auxiliary leg 68 of the left and the right lateral portions 38, 40 while the central curved portion 42 provides an abutment in the forward direction.

By lowering the central curved portion 42 below a plane defined by the two auxiliary legs 68, it is achieved that for a normal introduction of the hand-held apparatus into the support no contact between the end portion 30 of the light guide 24 and the central curved portion 42 is possible.

The lateral portion 40 is symmetrically embodied to the lateral portion 38 so that bracket 36 ends by an upwardly extending leg 70 having lower end 72.

In a modified embodiment it is suggested that the forward transition portion 44 is bent outwardly away from the axis of the hand-held apparatus 14. In this embodiment the transition portion between the upward legs 62, 70 and the forward transition portion 44 is located at the extension of the auxiliary leg 68 and forms the forward and lower support surface for the main body 18 of the apparatus 14. Starting at this support surface, the forward transition portions 44, in comparison to the representation of FIG. 2, are bent outwardly, i.e., radially away from the hand-held apparatus 14 so that even for a greatly rotated introduction of the angled end portion 30 of the light guide there is no risk that the end will catch.

Since, however, this type of introduction in practice is not very relevant, the shown embodiment of the inventive bracket 36 of FIG. 2 is preferred.

It is understood that the inventive bracket 36 can be inserted in the same manner into an additional stand or into the supply station 12. If needed, it is also possible to simply provide a bracket 36 which, as desired by the customer, i.e., the dentist, can be interchangeably inserted into the separate stand or the supply station 12.

According to a further preferred embodiment it is suggested that the support itself is a stand. In this embodiment, no additional stand is provided and the support can be removed from the supply station and placed onto any planar surface for storage. The support can, for example, be embodied such that it has three legs arranged such that even when the hand-held apparatus 14 is inserted, its stability is ensured.

FIG. 3 shows a possible embodiment of a stand 80. The auxiliary stand 80 receives the bracket 36 in cutouts 82 and 84 which are embodied as bores of sufficient depth in the downward direction and provide a stable supporting action. Preferably, the bores 82 and 84 have metallic sleeves which allow for a wear-resistant insertion and removal of the bracket 36 whereby fitting with respect to the leg 62 and 70 can be ensured without play.

In the shown embodiment the auxiliary stand 80 comprises a substantially flat, rectangular plate extending over the entire length of the light curing device 14 so that the end portion 30 of the light guide is positioned above the auxiliary stand 80 and does not project in the forward direction past the plate.

The stand 80 can be placed in any suitable manner onto a support surface. For example, it may embodied as a metal plate so that, because of its own weight, it provides sufficient stability. It is also possible to provide the stand 80 with suction cups which provide a secure storage on any table-like surface.

The present invention is, of course, in no way restricted to the specific disclosure of the specification and drawings, but also encompasses any modifications within the scope of the appended claims.

What is claimed is:

1. A curing device for light-induced curing of dental material, said curing device comprising:

a hand-held apparatus containing a light source, said hand-held apparatus being pistol-shaped and comprising a main body and a grip connected to said main body;

a supply station;

a stand separate from the supply station;

a cable connected to said grip for connecting said hand-held apparatus to the supply station; and a support for receiving said hand-held apparatus, said support being detachably connectable to the supply station or to the separate stand such that said support in which said hand-held apparatus is received is storable at the supply station or at the separate stand.

2. A curing device according to claim 1, wherein said support has a bracket for supporting at least a portion of said main body in front of said grip.

3. A curing device according to claim 2, wherein said bracket provides slanted supporting surfaces along both sides of said main body and beneath said main body.

4. A curing device according to claim 2, wherein said bracket includes two lateral portions and a curved center portion positioned between said lateral portions.

5. A curing device according to claim 4, wherein said length of said lateral portions is approximately half a length of said main body.

6. A curing device according to claim 4, wherein said grip is received and partly surrounded by said central curved portion.

7. A curing device according to claim 1, wherein said cable has plugs for detachably connecting said cable to the supply station and said grip.

8. A curing device according to claim 1, wherein said cable is provided in different lengths such that an appropriate length is selectable as needed.

9. A curing device according to claim 1, wherein said hand-held apparatus is positionable in said support only in one defined position and wherein said hand-held apparatus, when incorrectly placed into said support, will right itself relative to said support in order to assume said defined position.

10. A curing device according to claim 1, wherein said support when inserted into the stand is placeable onto a table.

11. A curing device according to claim 1, wherein the stand has a support plate extending beneath an end portion of a light guide of said curing device when received in said support.

12. A curing device for light-induced curing of dental materials, said curing device comprising:
   a hand-held apparatus containing a light source, said hand-held apparatus being pistol-shaped comprising a main body and a grip connected to said main body;
   a supply station;
   a stand separate from the supply station;
   a cable connected to said grip for connecting said hand-held apparatus to a supply station;
   a support for receiving said hand-held apparatus, said support having a bracket for supporting a least a portion of said main body in front of said grip, said bracket being comprised of a bent wire having two spaced apart ends removably insertable into a holder at the supply station or into the stand wherein said hand-held apparatus is storable at the supply station or separate from the supply station.

13. A curing device according to claim 12, wherein said hand-held apparatus comprises a light guide having an end portion angled downwardly.

14. A curing device according to claim 13, wherein said end portion of said light guide has an end face facing a surface of the supply station and positioned directly adjacent to the surface of the supply station when said hand-held apparatus is received in said support inserted into the holder.

15. A curing device according to claim 14, wherein between said surface of said supply station and said end face of said light guide a safety distance of 1 to 2 cm is provided.

16. An apparatus for light-induced curing of dental materials, said apparatus comprising:
   a supply station;
   a hand-held apparatus containing a light source;
   said hand-held apparatus being pistol-shaped comprising a main body and a grip connected to said main body;
   a cable connecting said grip of said hand-held apparatus to said supply station;
   a support for receiving said hand-held apparatus;
   said support detachably connectable to said supply station such that said support in which said hand-held apparatus is received is storable at said supply station or separate from said supply station.

17. A curing device for light-induced curing of dental materials, said curing device comprising:
   a hand-held apparatus containing a light source;
   said hand-held apparatus being pistol-shaped comprising a main body and a grip connected to said main body;
   a cable connected to said grip for connecting said hand-held apparatus to a supply station;
   a support for receiving said hand-held apparatus, said support having a bracket for supporting at least a portion of said main body in front of said grip, said bracket is comprised of a bent wire and has two lower ends, two lateral portions, and a curved center portion positioned between said lateral portions, when viewed from said ends' said bracket has two upwardly extending legs and first transition portions extending forwardly in a longitudinal direction of said main body, said lateral portions are connected to said first transition portions and extend to the rear of said main body parallel or diverging to said longitudinal direction, said bracket including two second transition portions extending downwardly and toward one another and connecting said lateral portions and said central curved portion;
   said support detachably connectable to the supply station or a stand such that said support in which said hand-held apparatus is received is storable at the supply station or separate from the supply station.

18. A curing device according to claim 17, wherein said lateral portions have a length between said first and second transition portions that is greater than a width of said grip in said longitudinal direction.

* * * * *

UNITED STATES PATENT AND TRADEMARK OFFICE
CERTIFICATE OF CORRECTION

PATENT NO. : 6,322,358 B1
DATED : November 27, 2001
INVENTOR(S) : Bruno Senn et al.

It is certified that error appears in the above-identified patent and that said Letters Patent is hereby corrected as shown below:

Column 9,
Line 15, change "4" to -- 18 --.
Line 51, change "a" (second occurrence) to -- at --.

Signed and Sealed this

Twentieth Day of August, 2002

Attest:

JAMES E. ROGAN
Attesting Officer    Director of the United States Patent and Trademark Office